(12) United States Patent
Cardarelli

(10) Patent No.: US 6,213,121 B1
(45) Date of Patent: Apr. 10, 2001

(54) NASAL FILTRATION SYSTEM

(76) Inventor: Venanzio Cardarelli, 20 N. Triangle Dr., Plymouth, MA (US) 02360

( * ) Notice: Subject to any disclaimer, the term of this patent is extended or adjusted under 35 U.S.C. 154(b) by 0 days.

(21) Appl. No.: 09/302,150

(22) Filed: Apr. 29, 1999

Related U.S. Application Data

(60) Provisional application No. 60/083,643, filed on Apr. 30, 1998.

(51) Int. Cl.$^7$ .................................................. A61M 15/08
(52) U.S. Cl. ................................. 128/206.18; 128/206.11
(58) Field of Search ........................... 128/206.11, 206.18

(56) References Cited

U.S. PATENT DOCUMENTS 4,327,719 * 5/1982 Childers ........................ 128/206.11
5,417,205 * 5/1995 Wang ............................. 128/206.11

* cited by examiner

Primary Examiner—John G. Weiss
Assistant Examiner—Mital Patel
(74) Attorney, Agent, or Firm—D. Michael Burns

(57) ABSTRACT

The present invention relates to a semi-removable nasal air cleaning system comprising of a surgically implanted portion including three sleeves implanted into the movable septum, a pair of stabilizer plates to distribute the stresses, and a septum stud deposed within the septum to support and orient the filter mediums. The septum supports a filtration means comprising of a connection component and a filter adapter component. The filters are easily retrievable when removal is necessary for cleaning or replacement.

17 Claims, 7 Drawing Sheets

NASAL FILTRATION SYSTEM

CROSS REFERENCE TO RELATED APPLICATION

This application is based on Provisional Patent Application Serial No. 60/083,643 filed Apr. 30, 1998.

BACKGROUND OF THE INVENTION

1. Field of the Invention

The present invention relates to a filtration system designed to be surgically implanted within the movable septum of the nasal passages. A system that allows the user to easily remove the filtering elements for cleaning or replacement. The system will purify the air before the air can reach the lungs.

2. Description of the Prior Art

Our lungs have drawn into them a huge volume of air during a lifetime. Along with the air come all manner of dusts, fumes, pollens, pollutants, viruses and gases. These often produce disease. There is a growing trend today whereby people are experiencing difficulty with their breathing, basically due to the poor quality of air. The quality of air is not improving and is extremely bad in the industrial regions of the world, especially Germany, Japan and the United States. Many inventions have focused on concerns of the air we breathe and the need to protect our respiratory systems. The nose is the primary portal for airborne transmission, especially viruses. While the nose is a remarkable organ and has always been a very efficient expeller of unwanted invaders, it has reached the point where it could use some additional help.

As air passes through the nose, three distinct functions are performed by the nasal cavities. First, the air is warmed by the extensive surfaces of the turbinates and septum; secondly, the air is moistened to a considerable extent, even before it passes beyond the nose; and thirdly, the air is filtered. For instance, if air was taken directly into the trachea without passing through the nose, the lungs would have to both cool and dry the air. This can lead to lung infection. We see the importance or the nose and its role in protecting the lungs. The hairs at the entrance to the nostrils are important because they remove the large particles. Much more important though is the removal of particles by turbulent precipitations which take care of particles down to the 4–6 micron range. Even though everyone is aware of the critical function of nose hairs, the public generally views them as unesthetic and thus cosmetically removes them which further adds to the problem.

The prior art is inundated with patents teaching of various ways to filter the air prior to its reaching the lungs. The prior art approaches this problem in two ways. One area of the prior art teaches the use of filtering and breathing devices that are used on the outside of the nose while another group discloses the utilization within the nose itself.

U.S. Pat. No. 5,636,629 issued to Paterson, Jr. on Jun. 10, 1997 discloses the use of a nasal glove. One that fits tightly on the exterior of the nose. Part of the device consists of a filter material that is porous and permeable to air, but not to small particles. The device is easily removed and carried on the user's person. Patterson, Jr. also teaches that the filter can be fabricated from a material selected from a group consisting of plastic, plastic components, fiberglass, plexiglass and other materials. Unlike the present invention, this invention is not designed to be used inside the nose.

The U.S. Pat. No. 5,611,333 issued to Johnson on Mar. 18, 1997, is part of a large art field which teaches the use of a dilator which is attached to the outside of the nose much like affixing a bandaid. These dilators work by separating outer wall tissues from inner structural tissues to dilate the nasal passages of the nose. While many athletes feel that these aid their breathing, they do not help in the filtration of particles before they reach the lungs, as does the present invention.

U.S. Pat. No. 5,568,808 issued to Rimkus on Oct. 29, 1996, teaches the use of a nose filter which is inserted into the nostril. It's easily positioned and removed. It's main function is to seal the nose so that all air must pass through the filtering element. This filter is kept in place by friction. It is not a permanently installed filter device as is the present invention.

U.S. Pat. No. 5,485,836 issued to Lincoln on Jan. 23, 1996, teaches of an air filter worn on the nose and affixed by an adhesive strip.

U.S. Pat. No. 5,392,773 issued to Bertrand on Feb. 28, 1995 teaches the use of a respiratory particulate filter which is adhered to the nose by an adhesive and the filter covers the opening to the nostrils.

U.S. Pat. No. 4,573,461 issued to Lake on Mar. 4, 1986 teaches of a nasal sealer and filter. The device is ellipsoidal in shape and made of a soft pliable impervious material when it is to be used as a sealer but, of a porous material when used as a filter. This device is strictly designed for temporary use.

U.S. Pat. No. 3,145,711 issued to Beber on Aug. 25, 1964, teaches a disposable nasal filter which easily is inserted into the nostril but is not semi-permanently implanted as is the present invention.

U.S. Pat. No. 2,192,093 to Moore, U.S. Pat. No. 2,151,227 to Pawelek, U.S. Pat. No. 1,071,015 to Adler, U.S. Pat. No. 390,027 to Locke and U.S. Pat. No. 142,477 to James are all shown as examples of how long a period of time inventors have been trying to filter air prior to its reaching our lungs.

None of the above inventions and patents taken either singly or in combination is seen to describe the instant invention as claimed.

SUMMARY

The present invention relates to a filtration system which is designed to be surgically implanted into the movable septum of the nose to aid in filtering the air we breathe. The present invention provides for a semi-permanent, removable and retrievable fixture having expendable filters. These may be removed by the user for cleaning or replacement and can be used for prolonged periods without discomfort. They can even be worn in the workplace, and also for routine daily activities in and out of the home. There is no need to remove them while sleeping.

The present invention has trans-septal cartilagenous components surgically implanted into the anterior-vestibular area of the movable septum. Depending on the size and angulation of the naris opening, the systems can be vary in size. The implanted portion, which is in permanent contact with the tissue, will be preferably gold or titanium, however other materials that are compatible with the tissue may be used.

The trans-septal cartilagenous components include a retention sleeve assembly, which is comprised of one large hexagonal shaped sleeve and two smaller circular shaped sleeves. These sleeves are maintained in a spatial relationship to each other by an orientation bar which orients all three sleeves to one another.

A septum stud is passed through the larger hexagonal sleeve, this stud comprising of two parts. The two parts are snap-fitted together and have outer extremities which are hexagonal in shape. A stabilizer device reinforces the septum, while maintaining the septum stud in the desired position. This stabilizer device is comprised of a pair of stabilizer plates which are locked together by securing rods that pass through the smaller sleeves of the retention sleve assembly. Slip-fitted over the ends of the septum stud are a pair of connecting components with a variety of arm lengths and angulations. These connecting components support filtering components which include grids and filters that are removably connected to the grids. The filters can be easily removed for cleaning or replacement by the user.

Accordingly, it is a principal object of the invention to provide a nasal filtration system which may be inserted directly into the nostril passages to prevent the flow of dust, viruses, bacteria, pollens or other foreign floating particles from entering the lungs upon inhalation.

It is another object of the invention to provide a breathing aid for sufferers of asthma, hay fever and other sinus problems.

It is a yet another object of the invention to provide a system that is professionally and surgically implanted by the Ear, Nose and Throat specialist or other trained specialist.

It is a further object of the invention to provide a nasal filter which is simple in construction, so that the user can easily remove the filter element for either cleaning or replacement.

It is still another object of the invention to provide a system that allows for implantation at various positions of the movable septum. Also, a system which is both readily adjustable to fit the particular contours of various patients while also being easily retrievable.

Still another object of the invention is to provide a nasal filter that is made of non-toxic, non-irritating parts which can be inserted and allowed to be in contact with the mucous membranes; without fear of damage or harm thereto and which will not impede with the volume of air that the person inhales.

It is another object of the invention to provide a new and improved filter system that is adapted to be inserted within the nostril whereby it will be fully seated, and for cosmetic reasons, concealed from view.

It is yet another object of the invention that the placement site for the system will allow the continuous free expressions of the nose for laughter, facial expression, flexibility of motion as well as the processes of sneezing and blowing of the nose.

These and other objects of the present invention will become readily apparent upon further review of the following specifications and drawings.

DETAILED DESCRIPTION OF THE PREFERRED EMBODIMENT

Figure 1:
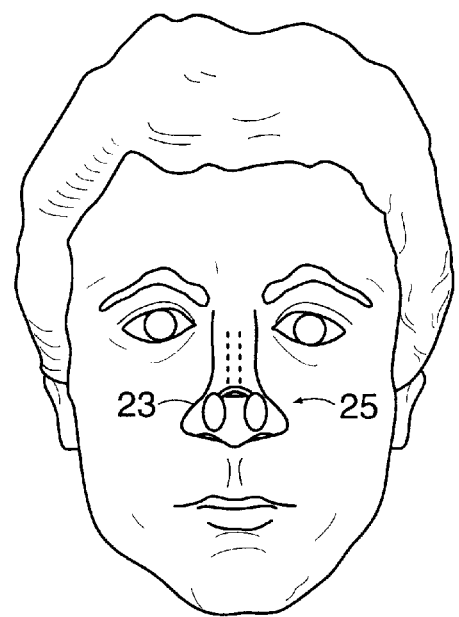
FIG. 1 is an environmental view of the nasal filtration system installed in the nasal passages of a person.

The present invention, as referred to in FIG. 1, shows an internally inserted nasal filtration system 25 which is surgically implanted into the movable septum 24 of a person's nose 23. The system 25 is surgically and semi-permanently implanted and is easily retrievable by the user.

Figure 2:
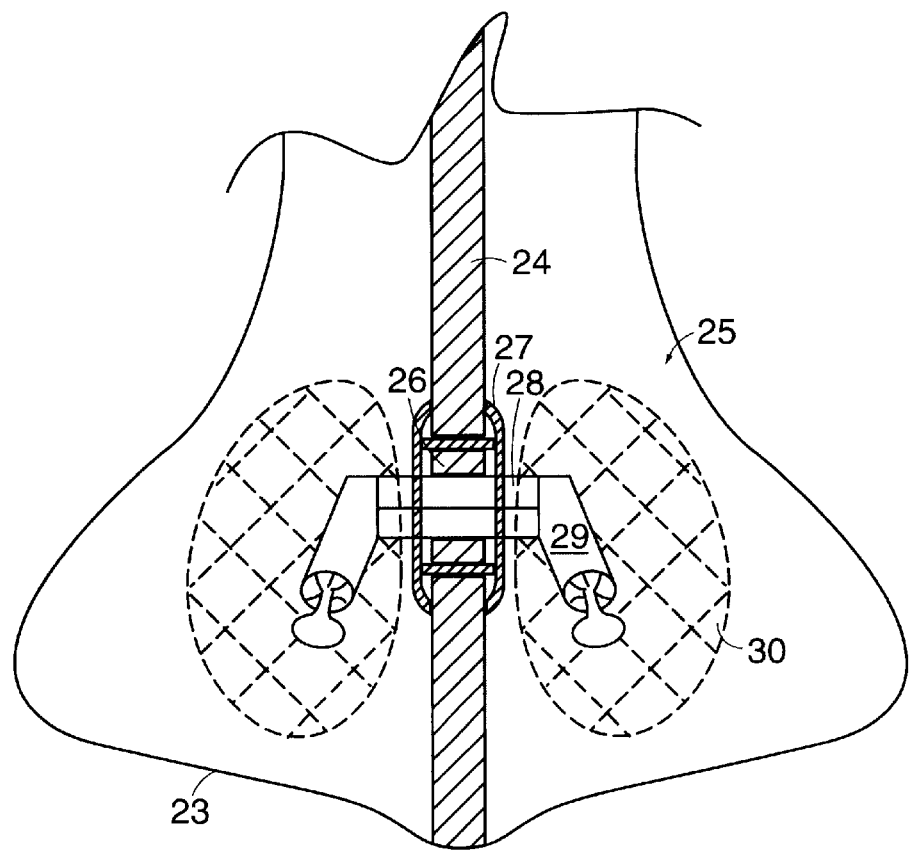
FIG. 2 is a prospective view of the nasal filtration system.

Prior to the device being implanted, the surgeon will make three perforations into the septum 24. These consists of two small and relatively round holes plus a larger, generally hexagonally shaped hole interposed between the two smaller ones. FIG. 2 shows the system 25 fully seated into the septum 24. The system 25 comprises a retention sleeve assembly 26, a stabilizer device 27, a septum stud 28, a connecting component 29 and a filtering component 30.

Figures 3, 3A:
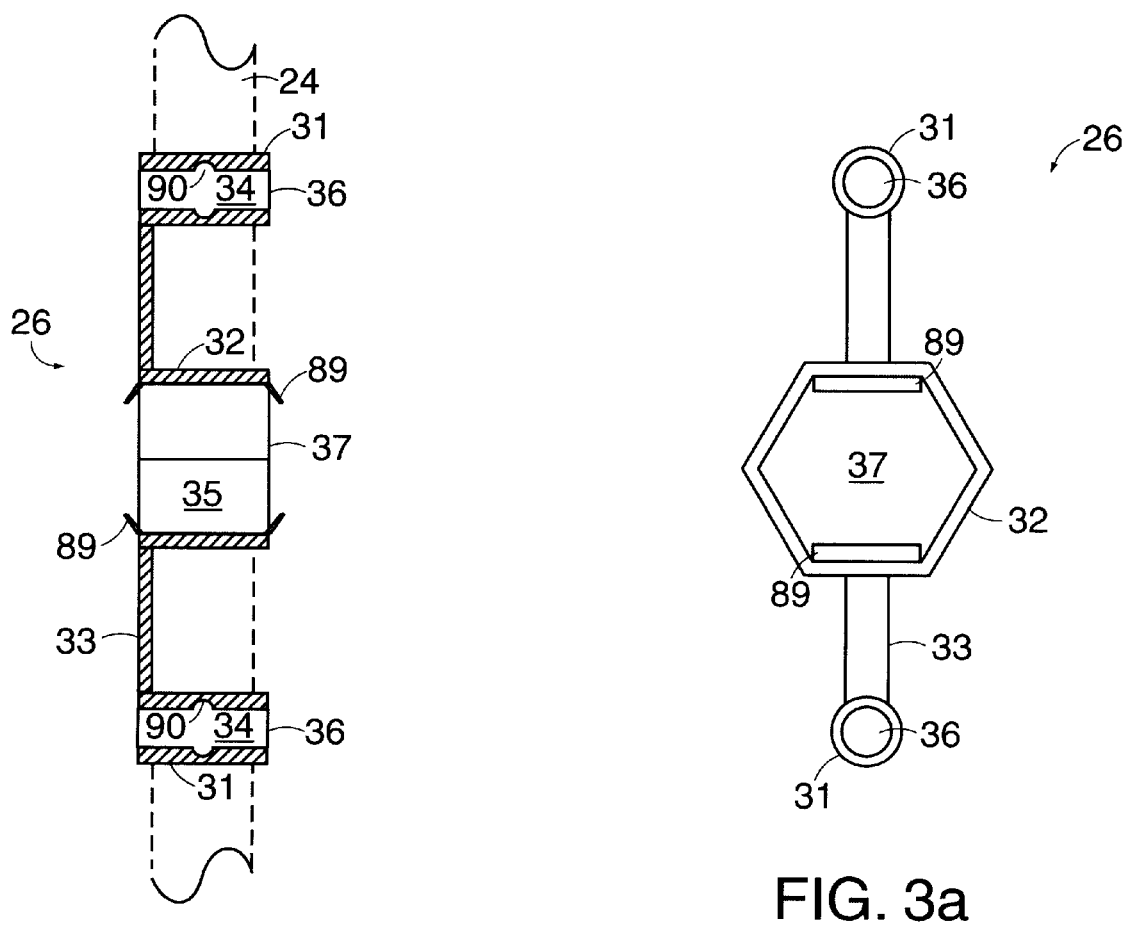
FIG. 3 is an elevational cross sectional view of the retention sleeve assembly.
FIG. 3a is a side view of the retention sleeve assembly shown in FIG. 3.

The retention sleeve assembly 26, depicted by FIGS. 3 and 3a, includes two relatively small hollow sleeves 31, each having an interior surface defining a circularly shaped passage 34. The sleeves 31 have circular apertures 36 which have their outer edges beveled to allow easy insertion and retention. Also included is a larger hollow sleeve 32 which has an inner surface defining a hexagonally shaped passage 35 and open ends 37 which are beveled. The sleeves 31 and 32 fit transversely through the surgical perforations and extend slightly beyond (on both sides) the dimensions of the septum 24. The sleeves 31 each have a circular recessed cavity 90 located at about the midpoint of the interior passage 34. To avoid any "drifting" of the sleeves 31 and 32 while in the septum 24, they are held together in a spatial relationship, fixed to each other by an orientation bar 33. The larger sleeve 32 has a pair of retention clips 89 at each opening 37. These clips 89 are located on the upper and lower sides of the hexagon opening 37. The sleeves 31 and 32 will be made of materials such as gold or titanium. Other materials known to be compatible with human tissue, may be used to avoid irritation and infection.

Figure 4:
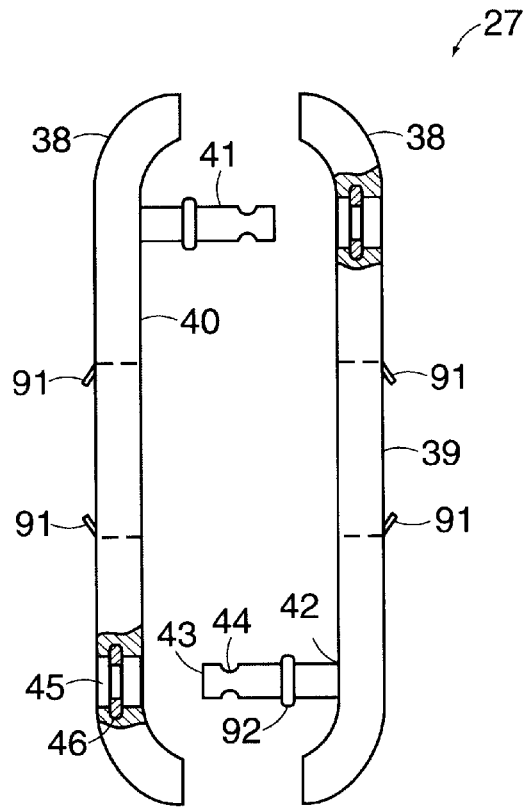
FIG. 4 is an elevational cross sectional view of the stabilizer device.
Figure 4A:
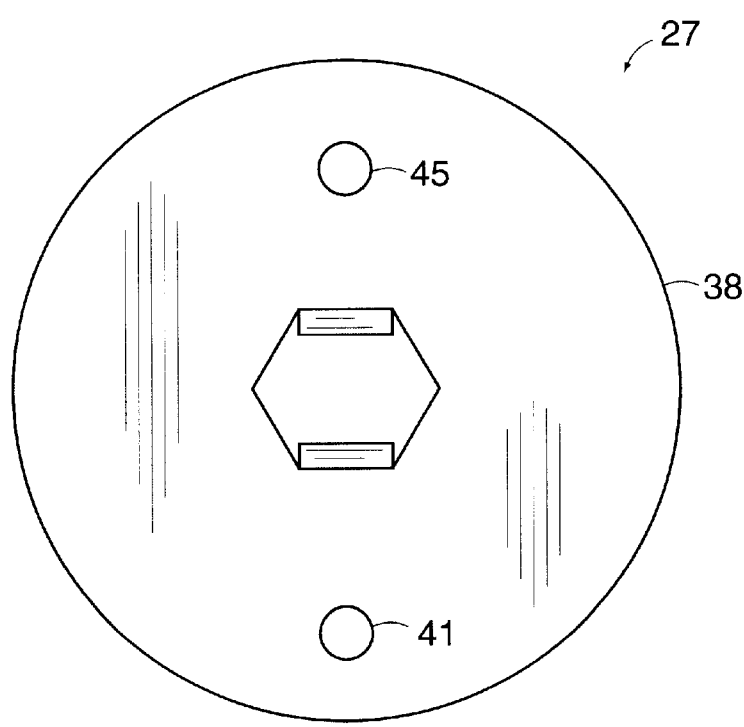
FIG. 4a is a side view of the stabilizer device.

Referring to FIG. 4, which shows the stabilizer device 27 to include a pair of stabilizer plates 38. The plates 38 are generally round, each having a hexagonally shaped opening 39 in their center areas for housing the passage of the septum stud 28. Located on two outer sides of the opening 39 and on the external surface of the plates 38 are stabilizing clips 91 which are similar to the retention clips 89 on the retention sleeve assembly 26. The plates 38 have an interior surface 40 and each plate 38 has, extending transversely in a perpendicular direction from the plate 38, a round securing rod 41. Each securing rod 41 having opposing ends, a proximal end 42 integral with the internal surface 40 and a distal end 43. A circular depressed groove 44 is located in close proximity to each distal end 43. The securing rods 41 each have a circular node 92 protruding at approximately the midpoints of the rods 41. The plates 38 each have an insertion hole 45 defined within their internal surface 40. The insertion holes 45 further having a crevice containing a raised ring 46 seated therein. The stabilizer device 27 is complete when the two plates 38 are manually pushed together with the securing rods 41 each passing through the small sleeves 31, whereby the circular nodes 92 slip-fit into the circular recessed cavities 90 of the sleeve channels 34 and the raised rings 46 are deposed into the depressed grooves 44.

Figure 5:
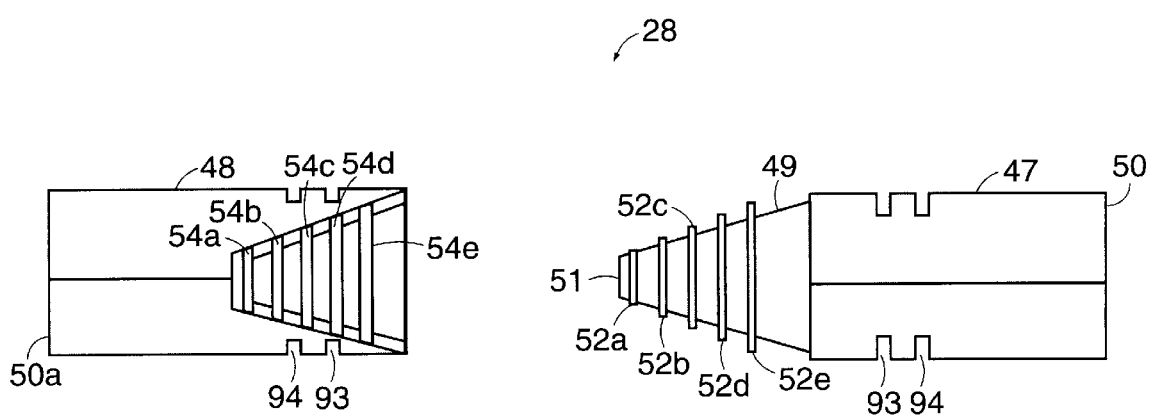
FIG. 5 is an expanded view of the septum stud.

Referring to FIG. 5 for a description of the septum stud 28, which includes a male member 47 and a female member 48. The male member 47 comprising two ends; one end having a tapered portion 49 and the other end a hexagonally faceted end 50. The tapered portion 49 having an insertion end 51 with five raised lips, a first lip 52a, a second lip 52b, a third lip 52c, a fourth lip 52d and a fifth lip 52e thereupon. The female member 48 of the stud 28 comprises one end having a tapered opening with five concave and circular channels a first channel 54a, a second channel 54c, a fourth channel 54d and a fifth channel 54e which are defined within the interior surface of the opening. The opposite end of the female member 48 is a hexagonal faceted section 50a, identical to the faceted end section 50 of the male member 47. Both members of the septum stud 28 are snap-fitted together and are deposed within the large hexagonal shaped passage 35 of the large sleeve 32. They are joined together by snapping the lips 52a, 52b, 52c, 52d and 52e into the channels 54a, 54b, 54c, 54d and 54e, thereby forming the stud 28 with an exterior surface comprising one unitary hexagonal surface. To insure that the stud 28 is correctly centered are four pair of notches, two pair of retention notches 93 and two pair of stabilizer notches 94, both deposed on two surfaces of the male and female members 47 and 48. When the members 47 and 48 are snapped together the two pair of retention notches 93 are mated with the clips 89 of the retention sleeve assembly 26 and the two pair of stabilizer notches 94 are mated with the stabilizing clips 91. Once in place within the larger sleeve 32, the septum stud 28 forms the basis of a central support for the system 25.

Figure 6:
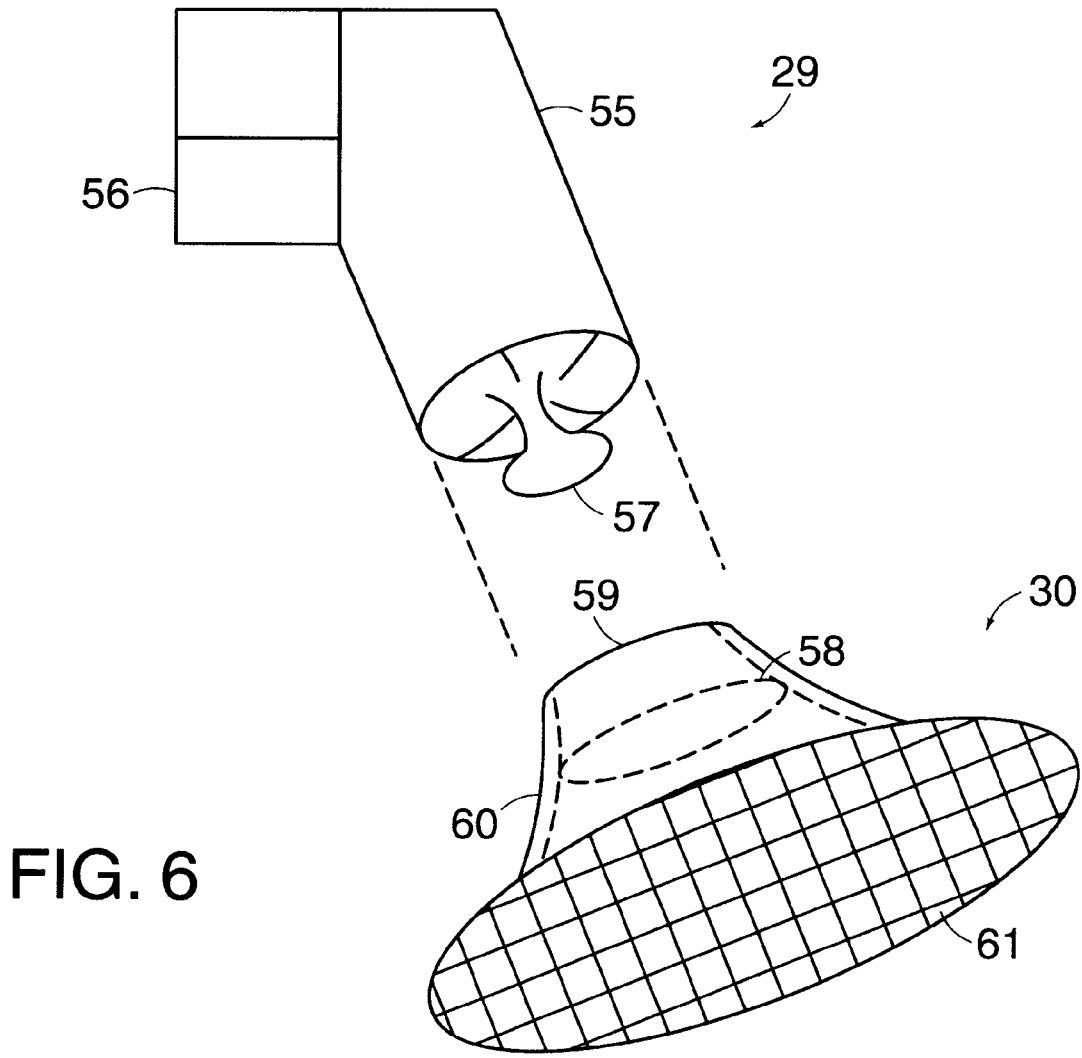
FIG. 6 is a perspective view of the connection means having an oval connector.

FIG. 6 illustrates the connecting components 29 of the preferred embodiment, each having a cylindrical extension arm 55 with a hexagonal slip-on opening 56 that is just large enough to slip over the hexagonal faceted ends 50 and 50a of the septum stud 28. The opposite end of the extension arm 55 is an elliptical shaped connector element 57. The connecting components 29 offer the most flexibility as relating to size, depth and angulation, which generally will be determined by the nose and filtration requirements of the user. The longer the extension arm 55, the closer the filter will be to the outer opening of the nose.

With the application of the filtering components 30 to the connector elements 57, which is shown in FIG. 6, the system 25 is in a completely functional mode. The filtering components 30 include adapter portions 58 which are located approximately at the center of an elliptically shaped filter 61. The adapter portions 58 have adaptor openings 59 which contain internally deposed adapter O-Rings slots 60. The user can slip-fit the filtering components 30 over the elliptical connector elements 57. The filtering components 30 generally will be of a measured size and will be retrievable and removable for cleaning or disposal. The materials can be plastic, rubber, titanium or gold. It is important that the filtering components do not impede the breathing process and that the material be compatible with the nasal tissues. The Ear, Nose and Throat specialist would measure and custom fit the patient. To aid in the cleaning of the air and killing of viral or bacterial invaders, the filter grids may be sprayed with surfactants which attract and also destroy these bacteria and antiviral agents. The filtering components 30 will be easily retrievable for cleaning and replacement.

Figure 7:
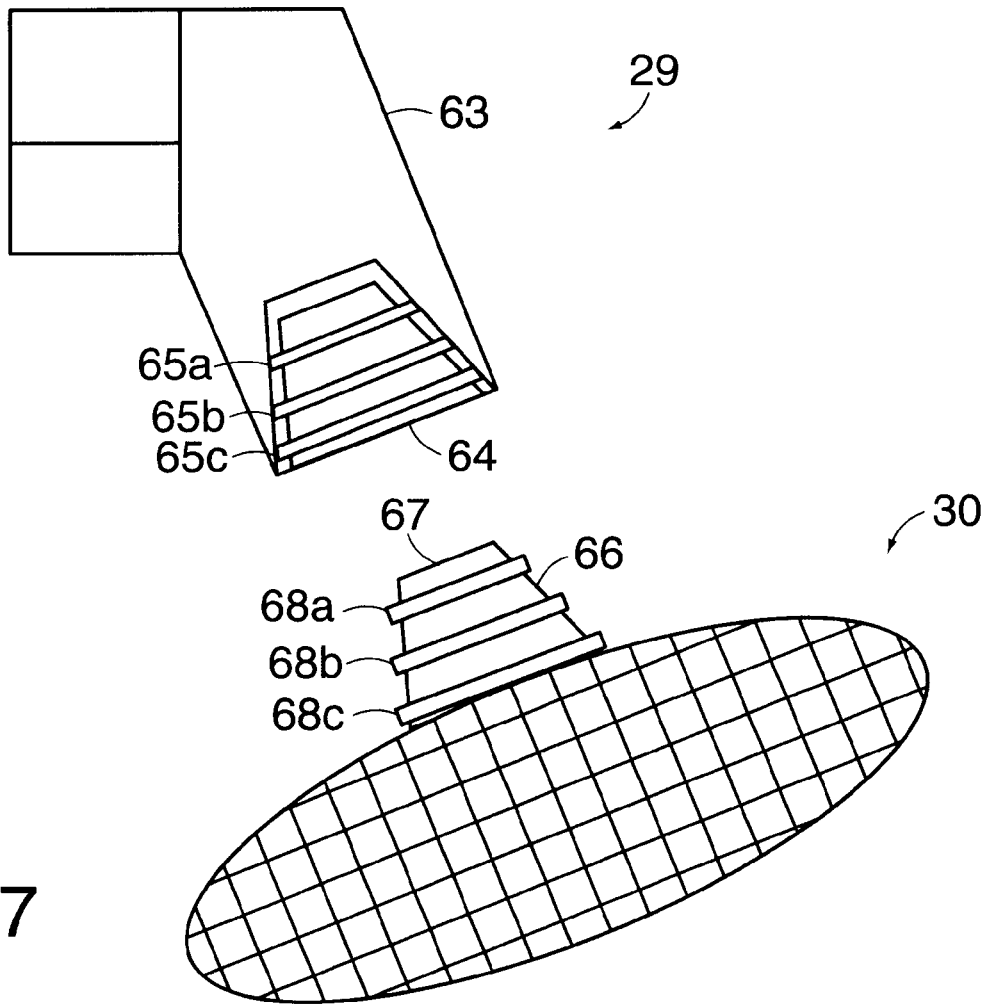
FIG. 7 is a sectional view of another embodiment of the connection means, one having a male-female connection.

Another embodiment is shown in FIG. 7, whereby the elliptical shaped connector elements 57 are replaced in the connecting components 29 with female connector section 63 which include tapered openings 64. Defined within the tapered openings 64 are three concave circumferential grooves a first groove 65a, a second groove 65b and a third groove 65c. This embodiment teaches another method for connecting the filtering components 30 to the connecting components 29. The filter elements 30, each have a male adapter portion 66, which includes a tapered adapter insertion part 67 comprising three raised ridges a first ridge 68a, second ridge 68b and a third ridge 68c. This embodiment is completed by snapping the insertion parts 67 into the tapered openings 64 to create a friction fit which is easily removable. This embodiment would appear to offer a more compact connection than that of the preferred embodiment. It still offers a very easy insertion and removal by the user. The materials of the connector sections 63 and adapters 66 can be metal, plastic or rubber.

Figure 8:
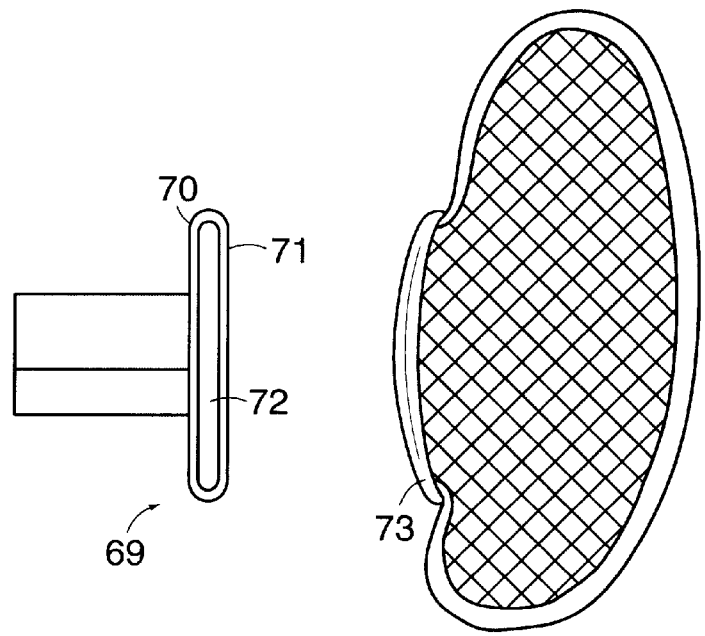
FIG. 8 is a sectional view of an embodiment having a connection means comprising a concave connection.

FIG. 8 depicts yet another embodiment. This would allow the filtering components 30 to be further into the nasal passages. This embodiment shows connecting components 29 that utilize concave connector elements 69 comprising of a convex upper surface 70 and a concave lower surface 71. The convex surface 70 being slightly higher than the concave wall 71 for easy insertion. Within the surfaces 70 and 71 are defined hollow concave conduits 72 made of materials that allow for easy penetration. The filtering components 30 include generally round adapter elements 73 that have a physical structure which is capable of being snapped into the hollow cancave conduits 72. The rounded adapters 73 can be metal or a hard plastic and must be able to maintain a rigid structure when being seated into position.

Figure 9:
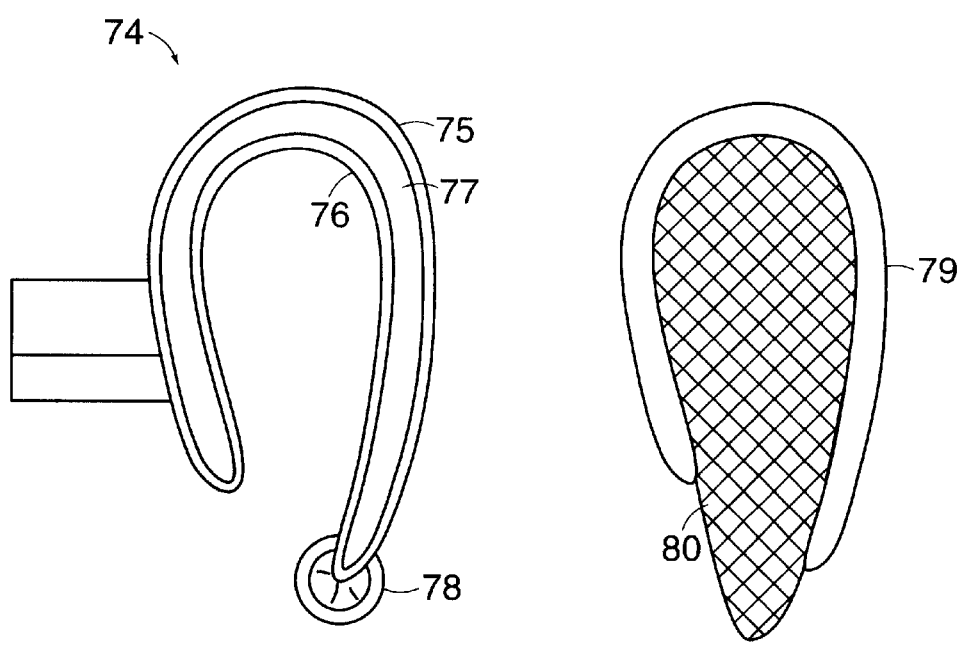
FIG. 9 is a sectional view of another embodiment, wherein the connection means comprises a U-shaped connector with corresponding filter element.

FIG. 9 shows a fourth option to the preferred embodiment, whereby the connecting components include horseshoe shaped connector elements 74, having a convex outer surface 75 and a concave inner surface 76. The surfaces 75 and 76 defining between them a horseshoe shaped conduit 77. The filtering components 30 have generally round adapter parts 79 capable of being snap-fitted into the conduits 77. The 79 contain replacable grids 80 which can be removed without the need to remove the entire filtration system 25. This embodiment provides the nose with rigid support for those who need it. It will also give the nose shape and help to keep the naris more open, which also increases the volume of air to the lungs. The horseshoe shaped connector elements 74 have soft pads 78 affixed at their distal ends to provide protection for the inner nose membranes.

It is to be appreciated that all the above connections could also be accomplished by using magnetized components. It is to be understood that the present invention is not limited to the embodiments described above, but encompasses any and all embodiments within the scope of the following claims.

| LEGEND | | |
|---|---|---|
| 23 | Human nose | |
| 24 | Septum | |
| 25 | Nasal filtration system | |
| | 26 | Retention sleeve assembly |
| | 27 | Stabilizer device |
| | 28 | Septum stud |
| | 29 | Connecting component |
| | 30 | Filtering component |
| | 26 | Retention sleeve assembly |
| | | 31 Small hollow sleeves (2) |
| | | 32 Large hollow sleeve |

-continued

LEGEND

| | | |
|---|---|---|
| | 33 | Orientation bar |
| | 34 | Circular interior passage of small sleeve |
| | 35 | Hexagonal interior passage of large sleeve |
| | 36 | Open ends of small sleeve |
| | 37 | Beveled open ends of large sleeve |
| | 89 | Retaining clips |
| | 90 | Circular recessed cavity |
| 27 | Stabilizer device | |
| | 38 | Round Stabilizer plates |
| | 39 | Hex opening in plates |
| | 40 | Internal surface of plates |
| | 81 | External surface of plates |
| | 41 | Securing rod |
| | 42 | Proximal end of rod |
| | 43 | Distal end of rod |
| | 44 | Depressed groove at distal end of rods |
| | 45 | Insertion hole |
| | 46 | Raised ring deposed within insertion hole |
| | 91 | Stabilizer clips |
| | 92 | Circular nodes |
| 28 | Septum stud | |
| | 47 | Male member of stud |
| | 48 | Female member of stud |
| | 49 | Tapered portion of male member |
| | 50 | Hexagonally faceted end of male member |
| | 50a | Hexagonally faceted end of female member |
| | 51 | Insertion end |
| | 52a | Raised lip on insertion end |
| | 52b | Raised lip on insertion end |
| | 52c | Raised lip on insertion end |
| | 52d | Raised lip on insertion end |
| | 52e | Raised lip on insertion end |
| | 53 | Tapered opening in female member |
| | 54a | Circular channels inside the tapered opening |
| | 54b | Circular channels inside the tapered opening |
| | 54c | Circular channels inside the tapered opening |
| | 54d | Circular channels inside the tapered opening |
| | 54e | Circular channels inside the tapered opening |
| | 93 | Retention notches on septum stud |
| | 94 | Stabilizer notches of septum stud |
| 29 | Connecting component | |
| | 55 | Extension arm |
| | 56 | Hexagon sleeve opening to fit over 50 and 50a |
| | 57 | Elliptical connector element |
| 30 | Filtering component | |
| | 58 | Adapter portion |
| | 59 | Adapter opening |
| | 60 | Adapter O-ring slot |
| | 61 | Elliptical shaped filter |
| | 62 | Filter grids for holding the filters |
| Embodiments | | |
| | 63 | Female connector element |
| | 64 | Tapered opening in female member |
| | 65a | Concave circumferential groove |
| | 65b | Concave circumferential groove |
| | 65c | Concave circumferential groove |
| | 66 | Male adapter portion |
| | 67 | Tapered insertion part |
| | 68a | Raised ridge |
| | 68b | Raised ridge |
| | 68c | Raised ridge |
| | 69 | Concave connector element |
| | 70 | Convex surface |
| | 71 | Concave surface |
| | 72 | Concave conduit |
| | 73 | Rounded adapter element |
| | 74 | Horseshoe shaped connector element |
| | 75 | Convex outer surface |
| | 76 | Concave inner surface |
| | 77 | Horseshoe shaped conduit |
| | 78 | Soft pad affixed to distal end |
| | 79 | Rounded adapter to fit into U-shaped connecter |
| | 80 | Horseshoe shaped removable filter |

I claim:

1. A nasal filtration system, in combination with three surgical penetrations defined within the anterior vestibular area of the movable septum, the system comprising:

a retention sleeve assembly including, three parallel hollow sleeves, a large sleeve and two smaller sleeves, the smaller sleeves parallel and flanking the larger sleeve, the sleeves tranversing through the three corresponding surgical penetrations, an orientation bar interconnecting the three sleeves and maintaining them in a spatial relationship to one another;

an elongated septum stud cointensively deposed within the larger sleeve for supporting the system, the stud having faceted opposing ends;

a stabilizer device including means for reinforcing the septum and maintaining the septum stud in the proper alignment and position within the septum; and means mounted to the hexagonal faceted opposing ends for filtering the inhaled air.

2. The nasal filtration system according to claim 2, wherein the surgical penetrations include:

a large hexagonally shaped penetration; and two smaller generally round penetrations on either side of the large penetration.

3. The nasal filtration system according to claim 3, wherein the retention sleeve assembly includes:

the large sleeve having an hexagonal exterior shape for cointensively being deposed within the large surgical penetration;

the large sleeve having an internal surface defining a hexagonally shaped passage, the passage supporting the septum stud; and the two smaller sleeves having a rounded shape and having internal surfaces defining round passages for accepting the stabilizer device.

4. The nasal filtration system according to claim 3, wherein the septum stud comprises:

hexagonally shaped male and female members; and means for releasable connecting the members with a friction type fit.

5. The nasal filtration system according to claim 4, wherein the reinforcing means of the stabilizer device includes:

a pair of stabilizer plates, each plate being in a relatively parallel relationship to each other;

each plate having defined a hexagonally shaped opening therein for deposing and supporting of the septum stud;

a pair of securing rods, each rod extending transversely from one of the plates in a perpendicular direction towards the other plate, the rods cointensively passing through and deposing within the small rounded sleeves of the retention sleeve assembly; and means for releasably securing the stabilizer device, the septum stud and the retention sleeve assembly, to each other.

6. The nasal filtration system according to claim 5, wherein the filtration means includes:

a pair of connecting components for removably mounting the filtering means to the faceted opposing ends of the septum stud; and a pair of filtering components, each component removably mounted to one of the connecting components, whereby the filtering means will be easily retrievable for cleaning and replacement.

7. The nasal filtration system according to claim 6, wherein each of the connecting components comprises:

an extension arm having opposing ends;

one end having defined therein a hollow sleeve opening for slipping upon one end of the septum stud; and an elliptically shaped connector element for releasably receiving the filtering component.

8. The nasal filtration system according to claim 7, wherein each filtering component comprises:

a filter;

a grid frame for releasably holding the filter; and an elliptically shaped adapter portion integral with the grid frame, the adapter having an opening defined therein for mounting to the connecting element, whereby the system is complete and the filtering component easily retrievable for cleaning or replacement.

9. A nasal filtration system designed for surgical implantation into the anterior vestibular area of the movable septum, the system comprising:

the septum having defined therein three surgical perforations, a large hexagonally shaped perforation flanked by two smaller generally round perforations;

a retention sleeve assembly having three longitudinally parallel sleeves, a large hexagonally shaped sleeve interposed between two smaller generally round sleeves, the sleeves cointensively transversing through the three correlating surgical penetrations, an orientation bar interconnecting the three sleeves and maintaining them in a spatial relationship to one another;

an elongated hexagonally shaped septum stud longitudinally and cointensively deposed within the larger sleeve, the stud having hexagonal faceted opposing ends;

a stabilizer device for reinforcing the septum and maintaining the septum stud in the proper alignment and position within the septum; and means for filtering the inhaled air, the means including:

a pair of connecting components for removably mounting the filtering means to the hexagonal faceted opposing ends of the septum stud; and a pair of filtering components, each filtering component removably mounted to one of the connecting components, whereby the filtering means will be easily retrievable for cleaning and replacement.

10. The nasal filtration system according to claim 9, wherein the retention sleeve assembly includes:

the small sleeves having interior surfaces defining at approximately the midpoint of each sleeve a circular recessed cavity; and wherein the stabilizer device includes:

a pair of generally round stabilizer plates, each plate being in a relatively parallel relationship to each other, each plate having an internal and an external surface;

a hexagonal opening defined between internal and external surfaces of each plate for passage thereof of the septum stud;

the internal surface of each plate defining an insertion hole, a raised ring being deposed within the hole;

a pair of round securing rods extending transversely from the internal surface of each plate perpendicularly towards the other plate, each rod to be cointensively deposed within the small round sleeves of the retention sleeve assembly, each rod having opposing ends, a proximal end integral with the internal surface of the plate, and a distal end;

defined in an area of close proximity to the distal end, a circular depressed groove for mating with the raised ring of the insertion hole; and a circular node protruding about the midpoint of each securing rod, for joining with the circular recessed cavity of each small sleeve, whereby the stabilzer device is capable of connecting together with the retention sleeve assembly at four releasable locking points, two at the insertion holes and the other two at the midpoints of the small sleeves, thereby providing for a secure yet releasable friction fit.

11. The nasal filtration system according to claim 10, wherein the septum stud comprises:

hexagonally shaped male and female members, the male member having an insertion end and the opposing end, the female member having an end defining a tapered opening and the opposing end;

a tapered portion extending from the insertion end of the male member, a plurality of raised lips dispersed thereupon;

the tapered opening having defined therein a plurality of circular channels deposed for accepting the plurality of lips of the male member, whereby the two portions can be releasably snapped together to complete the stud; and the opposing ends accepting the mounting of the connector components.

12. The nasal filtration system according to claim 11, wherein each of the external surfaces of the stabilizer plates includes a pair of stabilizer clips integral with two opposing sides of the hexagonal openings;

wherein the large hexagonal sleeve includes a pair of retention clips at each end of the sleeve, the clips being integral with two opposing sides of the hexagonal opening;

wherein the septum stud includes four pairs of notches defined upon two of the hexagonal surfaces, two pair of stabilizer notches for friction fitting with the stabilizer clips, two pair of retention notches for friction fitting with the retention clips, whereby the septum stud is maintained in the correct alignment and proper position within the system.

13. The nasal filtration system according to claim 12, wherein the connecting components of the filtration means each include:

an extension arm, the arm having opposing ends, one end defining a hexagonal hollow sleeve opening for slipping over the hexagonally faceted end of the septum stud, the other end a connector element; and wherein each filtering component includes:

a filter;

a grid frame for removably holding the filter; and an adapter portion integral with the grid frame, the adapter portion defining an opening therein for mounting to the connector element, whereby the system is complete.

14. The nasal filtration system according to claim 13, wherein each connector element is of an elliptical shape.

15. The nasal filtration system according to claim 13, wherein each connector element has defined therein a tapered female opening, the opening having defined therein a plurality of concave circumferential grooves to accept a cooperating adapter portion to complete the system.

16. The nasal filtration system according to claim 13, wherein each connector element is concave shaped, each element comprising:

a convex upper surface;

a concave lower surface; and defined between the surfaces, a concave conduit to accept a cooperating adapter part to complete the system.

17. The nasal filtration system according to claim 13, wherein each connector element has a horseshoe shape, each element comprising:

a convex outer surface;

a concave inner surface; and defined between the surfaces a horseshoe shaped conduit for accepting a corresponding adapter part, whereby the shape of the filter will provide the nostril with a measure of rigid support and will also keep the naris in a more open position which will allow for an increase in the volume of air to the lungs.

* * * * *